US00PP33502P2

(12) United States Plant Patent
Dibley

(10) Patent No.: US PP33,502 P2
(45) Date of Patent: Sep. 21, 2021

(54) ***BEGONIA* PLANT NAMED 'BDIBL12-0'**

(50) Latin Name: *Begonia rex-cultorum*
Varietal Denomination: BDIBL12-0

(71) Applicant: Dibley's Nurseries, Ruthin (GB)

(72) Inventor: Lynne Dibley, Ruthin (GB)

(73) Assignee: Dibley's Nurseries

( * ) Notice: Subject to any disclaimer, the term of this patent is extended or adjusted under 35 U.S.C. 154(b) by 0 days.

(21) Appl. No.: 17/115,945

(22) Filed: Dec. 9, 2020

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./343
See application file for complete search history.

*Primary Examiner* — Susan McCormick Ewoldt
(74) *Attorney, Agent, or Firm* — Cassandra Bright

(57) ABSTRACT

A new and distinct variety of *Begonia rex-cultorum* plant named 'BDIBL12-0' is disclosed, characterized by a large palmate foliage of greyed-green with a distinctive lavender and pink margin. Plants are large, upright and grow rapidly. The new variety is a *Begonia*, and is normally used as an ornamental garden or container plant.

1 Drawing Sheet

Latin name of the genus and species: *Begonia rex-cultorum.*

Variety denomination: 'BDIBL12-0'.

BACKGROUND OF THE INVENTION

The new cultivar is the product of a planned breeding program. The new variety originated as the result of a cross performed during 2018 of an unnamed, unpatented proprietary *Begonia rex-cultorum* as the seed parent, and the unpatented *Begonia rex-cultorum* 'Midnight Magic' as the pollen parent. The selection of the new variety was made during August of 2018 by the inventor at a research greenhouse located in Wales, UK.

Asexual reproduction of the new cultivar 'BDIBL12-0' was first performed at a research greenhouse located in Wales, UK by terminal vegetative cuttings in August of 2018. 'BDIBL12-0' has since produced three generations by vegetative cuttings and has shown that the unique features of this cultivar are stable and reproduced true to type.

SUMMARY OF THE INVENTION

The cultivar 'BDIBL12-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BDIBL12-0'. These characteristics in combination distinguish 'BDIBL12-0' as a new and distinct *Begonia rex-cultorum* cultivar:

1. Upright plant habit.
2. Palmate leaf.
3. Rapid growth.
4. Large plant.

5. Greyed-Green foliage with a distinctive lavender and pink margin.

PARENT COMPARISON

Plants of the new cultivar 'BDIBL12-0' are similar to plants of the seed parent variety in most horticultural characteristics. However, plants of the new cultivar 'BDIBL12-0' differ in the following:

1. Leaves of the new variety are larger than leaves of the seed parent.
2. Plants of the new variety have a shorter, less leggy habit than the seed parent.
3. Plants of the new variety grow faster than plants of the seed parent.

Plants of the new cultivar 'BDIBL12-0' are similar to plants of the pollen parent variety in most horticultural characteristics. However, plants of the new cultivar 'BDIBL12-0' differ in the following:

1. Leaves of the new variety are palmate, leaves of the pollen parent are cordate.
2. Plants of the new variety are taller than plants of the pollen parent.
3. Foliage of the new variety is greyed-green with a lavender and pink margin, foliage of the seed parent is dark green.
4. Plants of the new variety are not as susceptible to fungal infection as are plants of the pollen parent.
5. Foliage of the new variety is not as deeply rugose as foliage of the pollen parent.

COMMERCIAL COMPARISON

Plants of the new cultivar 'BDIBL12-0' are similar to plants of the commercial variety, *Begonia* 'BRXBR15-0' U.S. Plant Pat. No. 24,110 in most horticultural characteristics. Plants of the new cultivar 'BDIBL12-0' differ in the following:

1. Foliage of the new variety has a jagged margin not found on 'Rothko'.
2. Foliage of the new variety is greyed-green with a lavender and pink margin, foliage of 'Rothko' is red with black margins.
3. Plants of the new variety are shorter than plants of this comparator.

Plants of the new cultivar 'BDIBL12-0' are similar to plants of the commercial variety, *Begonia* 'Bewitched White', unpatented, in most horticultural characteristics. However, plants of the new cultivar 'BDIBL12-0' differ in the following:

1. Foliage of the new variety has a darker coloration throughout.
2. Foliage of the new variety has a distinctive lavender and pink margin pattern that grows more vivid and darker. In comparison, foliage of 'Bewitched White' is a lighter color throughout the leaf.

BRIEF DESCRIPTION OF THE PHOTOGRAPH

The present invention of a new and distinct variety of *Begonia* is shown in the accompanying photograph, the colors being as nearly true as possible with color photographs of this type. Age of the plant is approximately 16 weeks, shown in a 1 gallon pot.

DETAILED BOTANICAL DESCRIPTION

In the following description, color references are made to The Royal Horticultural Society Colour Chart 2007 except where general terms of ordinary dictionary significance are used. The following observations and measurements describe 'BDIBL12-0' plants grown in a commercial controlled greenhouse in Santa Paula, Calif. Measurements and numerical values represent averages of typical plant types.

Botanical classification: *Begonia rex-cultorum* 'BDIBL12-0'.

Age of plant described: Approximately 12 weeks.

Container of plant described: 6-inch pot.

Propagation:

Type of propagation typically used: Vegetative tip cuttings.

Time to develop roots: About 10 days at approximately 21° C.

Time to develop a rooted liner: About 21 days at approximately 21° C.

Root description: Fibrous, fine, well branched. White and tan, not accurately measured with the R.H.S. chart.

Plant:

Growth habit: Upright growing, fleshy annual.

Plant shape: Upright, flattened globular.

Pot size of plant described: 6-inch.

Height: Approximately 38 cm.

Plant spread: Approximately 42 cm.

Growth rate: Rapid.

Branching characteristics: Basally emerging foliage, no actual branches, only petioles.

Foliage:

*Type*.—Single, basally emerging foliage and long petioles.

*Orientation*.—Mainly upwardly facing foliage. Lower, oldest foliage outwardly facing.

*Strength*.—Very strong, hard foliage, resists breakage.

*Texture, top surface*.—Leathery, slightly rugose along main vein. Moderately hirsute throughout blade.

*Texture lower surface*.—Main surface non-pubescent, veins sparsely hirsute. Largest veins more densely hirsute.

*Appearance*.—Metallic, matte and slightly leathery appearance to upper surface. Lower surface matte.

*Quantity*.—Approximately 22 to 28.

*Shape of blade*.—Overall palmate.

*Apex*.—Acute.

*Base*.—Cordate, very slightly overlapping top of leaf surface.

*Margin*.—Incised and serrate. Sinuses acute, average depth approximately 1.5 to 3.5 cm.

*Aspect*.—Mainly flat, slight upward fold.

*Mature leaves*.—

*Average length*.—Average range 12 to 18 cm.

*Average width*.—Average range 12 to 16 cm.

*Color*.—Mature foliage upper side: Main color near Greyed-Green 189B with sheen near 191D. Center blotch, approximately 20% of leaf blade RHS Greyed-Purple 187A. Well defined margin colored near Greyed-Purple N187A and N187B, interior edge of margin tinged Greyed-Purple 186B. Purple marginal coloration increases with maturity. Mature foliage under side: Main color near Greyed-Green 191C. Center blotch, approximately 10% of leaf blade RHS Greyed-Purple 187A. Well defined margin colored near Greyed-Purple N187A and N187B, interior edge of margin tinged Greyed-Purple 186C. Purple marginal coloration increases with maturity. Venation: Type: Palmate. Venation color upper side: Near Greyed-Green N189A. Venation color under side: Near Greyed-Green N189A.

*Petiole*.—Length: Average range 10 to 15 cm. Diameter: Approximately 6 to 8 mm. Color: Background color near RHS Greyed-Green 191B, completely flushed Greyed-Purple N187A. Texture: Hirsute.

*Stipule description*.—Length: Approximately 1.0 cm. Diameter: Approximately 1.0 cm. Shape: Deltate. Apex: Acute. Base: Truncate. Color: Immature near RHS Greyed-Purple N187B, upper and lower surfaces. Dries to Grey-Brown 199B, upper and lower surfaces, before leaf matures. Texture: Upper Surface: Very sparsely pilose. Lower Surface: Glabrous.

Flower: Not observed to date.

Reproductive organs: Not observed to date.

Other characteristics:

Seeds and fruits: Not observed to date.

Disease/pest resistance: Neither resistance nor susceptibility to diseases or pests of *Begonia* has been observed in this variety.

Temperature tolerance: The new variety tolerates temperatures from approximately 5° to 35° C.

What is claimed is:

1. A new and distinct cultivar of *Begonia rex-cultorum* plant named 'BDIBL12-0' as herein illustrated and described.

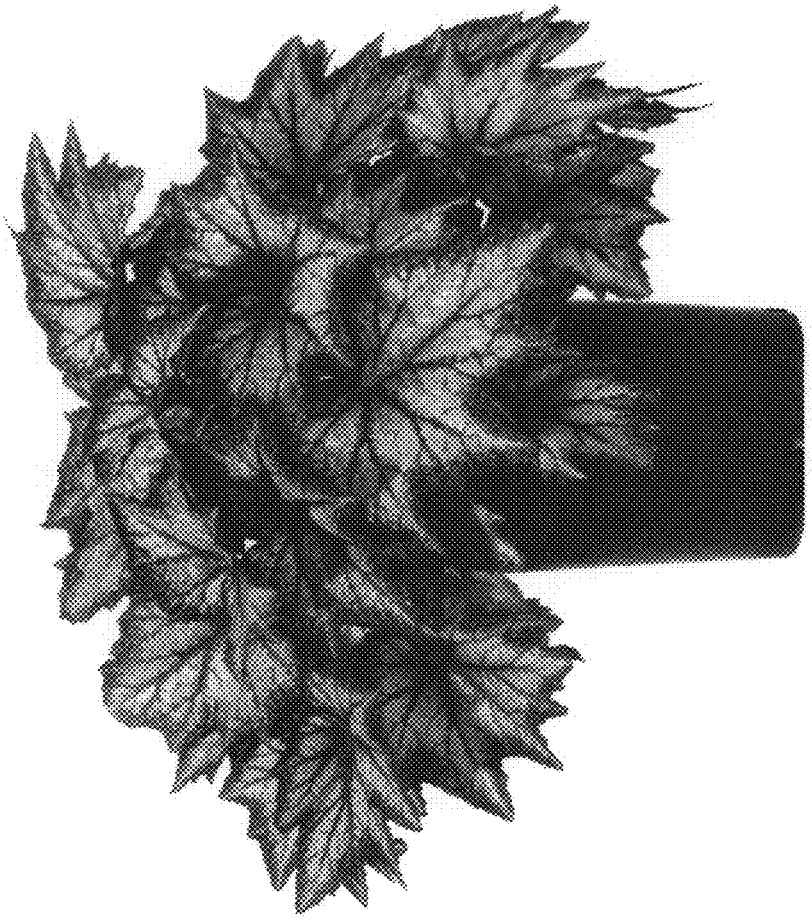

* * * * *